United States Patent
Rübben

(10) Patent No.: US 9,907,935 B2
(45) Date of Patent: Mar. 6, 2018

(54) COATING OF BALLOON CATHETERS

(71) Applicant: Alexander Rübben, Monaco (MC)

(72) Inventor: Alexander Rübben, Monaco (MC)

(73) Assignees: Alexander Rübben, Monaco (MC); Aachen Scientific International PTE. LTD., Singapore (SG)

( * ) Notice: Subject to any disclaimer, the term of this patent is extended or adjusted under 35 U.S.C. 154(b) by 133 days.

(21) Appl. No.: 14/404,643

(22) PCT Filed: Jun. 3, 2013

(86) PCT No.: PCT/EP2013/061352
§ 371 (c)(1),
(2) Date: May 22, 2015

(87) PCT Pub. No.: WO2013/178820
PCT Pub. Date: Dec. 5, 2013

(65) Prior Publication Data
US 2015/0258311 A1    Sep. 17, 2015

(30) Foreign Application Priority Data
Jun. 1, 2012    (DE) .................. 10 2012 010 800

(51) Int. Cl.
*A61M 25/10* (2013.01)
*A61L 29/16* (2006.01)
*A61L 29/08* (2006.01)

(52) U.S. Cl.
CPC ....... *A61M 25/1029* (2013.01); *A61L 29/085* (2013.01); *A61L 29/16* (2013.01);
(Continued)

(58) Field of Classification Search
CPC .. A61M 2025/1031; A61L 29/16; A61L 29/08
(Continued)

(56) References Cited

U.S. PATENT DOCUMENTS 5,102,402 A    4/1992   Dror et al.
6,129,705 A   10/2000   Grantz
(Continued)

FOREIGN PATENT DOCUMENTS

DE    102007003184 A1   7/2008
DE    102008034826 A1   1/2010
WO    2010/009904 A2    1/2010

OTHER PUBLICATIONS

Bouchard et al. Properties of Sugar, Polyol, and Polysaccharide Water-Ethanol Solutions. J. Chem Eng Data 2007 vol. 52 pp. 1838-1842.*
(Continued)

*Primary Examiner* — Cachet I Sellman
(74) *Attorney, Agent, or Firm* — Gudrun E. Huckett

(57) ABSTRACT

The invention relates to a method for coating the balloon of a balloon catheter, wherein the surface of the balloon is at least partially wetted with a first solution of an active ingredient, the part of the surface of the balloon wetted with the first solution of the active ingredient is wetted with a liquid containing water and/or at least one alcohol, and the part of the surface of the balloon wetted with the first solution and the liquid containing water and/or at least one alcohol is wetted with an additional solution that contains a polysaccharide. In this way, the balloon is provided with an active ingredient layer, which during the balloon dilatation is effectively applied to the vessel inner wall due to the embrittlement of the surface and cases a slowed, long lasting release of the active ingredient.

14 Claims, 1 Drawing Sheet

(52) U.S. Cl.
CPC ... *A61L 2300/602* (2013.01); *A61L 2300/606* (2013.01); *A61L 2420/02* (2013.01); *A61L 2420/06* (2013.01); *A61M 2025/105* (2013.01); *A61M 2025/1031* (2013.01)

(58) Field of Classification Search
USPC ....... 427/2.24–2.25, 2.28; 604/103.02, 96.01
See application file for complete search history.

(56) References Cited

U.S. PATENT DOCUMENTS

| | | | |
|---|---|---|---|
| 2004/0234575 A1* | 11/2004 | Horres | A61K 31/727 424/426 |
| 2007/0065481 A1* | 3/2007 | Chudzik | A61K 9/0024 424/426 |
| 2009/0024200 A1* | 1/2009 | Wilcox | A61L 31/10 623/1.11 |
| 2010/0145266 A1* | 6/2010 | Orlowski | A61L 29/08 604/96.01 |
| 2011/0190696 A1* | 8/2011 | Rubben | A61L 29/16 604/96.01 |

OTHER PUBLICATIONS

Physical Properties of Dextran. retreived from http://www.dextran.net/about-dextran/dextran-chemistry/physical-properties.aspx May 15, 0217.*

* cited by examiner

*Translation of labels in figure: Acceleration voltage - working distance - magnification*

COATING OF BALLOON CATHETERS

BACKGROUND OF THE INVENTION

The invention relates to a method for coating the balloon of a balloon catheter, wherein the surface of the balloon is wetted at least partially with a first solution of an active agent and said part of the surface of the balloon wetted with said first solution of an active agent is wetted with a liquid containing water and/or at least one alcohol. Moreover, the invention relates to the balloon and the balloon catheter itself.

In medicine, so-called "minimally invasive procedures" play an ever increasing role. Percutaneous transluminal angioplasty (PTA) by means of balloon dilatation is frequently employed for the treatment of vasoconstrictions such as arteriosclerosis. For this purpose, a balloon catheter provided in its distal area with a balloon inflatable by the infeed of a fluid is brought to the stenotic site (vasoconstriction) with the help of a guide catheter. At the stenotic site the balloon is inflated causing deposits/plaque inhibiting the flow of blood to be pressed against or into the vessel wall so that unhindered perfusion is restored. To rule out the reoccurrence of such a vessel constriction a stent may often be implanted to keep the vessel open. After collapsing of the balloon the balloon catheter is withdrawn and removed from the vascular system whereas a stent that may have been implanted will remain in the vessel.

Within the framework of angioplasty the vessel, however, may again suffer constriction (restenosis) after the balloon catheter has been removed, which is due to the proliferation of cells, i.e. cells grow into the vessel lumen and again impede the free flow of blood. To prevent this undesirable effect, balloon catheters coated with medical substances are employed, which enables such a substance to be applied to the inner wall of the vessel at the location where stenosis has occurred, with said medical substance usually having a proliferation-inhibiting effect that shall prevent restenosis.

Typically, an active substance dissolved in a solvent is applied to the surface of the balloon, with the solvent subsequently evaporating. The active agent is present in the form of a layer on the surface and can be applied while balloon dilatation takes place. In this context, adherence of the active agent on the balloon has turned out to be problematic.

In publications U.S. Pat. No. 5,102,402 and U.S. Pat. No. 6,129,705 for example it has been described how the adherence of an active agent on the surface can be improved. Publication U.S. Pat. No. 5,102,402 provides elucidation of a balloon catheter coated with medical substances. In a first variant thereof microcapsules filled with an active agent or drug are enclosed in folds in the balloon surface and in this way are mechanically retained in their relevant positions. In a second variant the microcapsules are attached to the balloon surface with the aid of an adhesive.

In publication U.S. Pat. No. 6,129,705 a balloon catheter has been described the surface of which is provided with a coating into which the microcapsules filled with an active agent are completely embedded. It is to be noted, however, that filling the active agent into microcapsules and subsequently attaching the microcapsules to or embedding them in the surface of the balloon are comparatively sophisticated and thus expensive processes.

In principle, it is desirable for the surface of the balloon of the balloon catheter to be provided with a homogenous and reproducible load of medical substances and also release the drugs to the surrounding tissue in the body in a uniform manner.

As per a method explained in detail in WO 2010/009904 A2 the surface of the balloon shall initially be treated with a first solution of the active agent and subsequently treated with a second solution of the same active agent. In this way, a more brittle, chalk-like surface is created that results in an improved release of the active agent when the balloon is pressed against the inner wall of the vessel to be treated, as compared with surface coatings produced through a treatment with only a first solution.

In the past, problems were encountered, however, in that a significant amount of the active agent was carried away by the blood stream either at the time the balloon catheter was inserted into the blood vessel or within a relatively short period thereafter and thus was no longer available to fulfill the intended purpose. After the balloon catheter has been removed the release of the active agent diminishes very quickly.

It is therefore the object of the invention to provide a method for coating the balloon of a balloon catheter, respectively a balloon/balloon catheter, by means of which an improved long-term effect can be achieved.

SUMMARY OF THE INVENTION

In accordance with the invention, this object is solved by a method for coating the balloon of a balloon catheter, wherein the surface of the balloon is wetted at least partially with a first solution of an active agent, said part of the surface of the balloon wetted with said first solution of an active agent is wetted with a liquid containing water and/or at least one alcohol, and said part of the balloon surface wetted with the first solution and the water and/or at least one alcohol containing liquid is wetted with a further solution that contains a polysaccharide.

Using the inventive balloon catheter involves the catheter being introduced into the blood vessel system and then inflated and in this way pressed against the inner wall of the vessel. During this process a large portion of the coating is transferred onto the inner vessel wall. After deflation and removal of the balloon catheter from the vessel system the active agent provided within the coating gradually penetrates into the vessel tissue, wherein active agent concentrations were found to be present in the vessel tissue treated even 48 h after dilatation of the balloon that still corresponded to 10 to 50%, preferably at least 20% of the concentration that existed 2 h after the treatment, which could be proved in animal experiments on pigs.

Surprisingly, it has been found that the polysaccharide coating has an effect on the inner wall of the treated vessel like glue or adhesive, resulting in the active agent to adhere significantly better to the vessel wall and be less easily carried away by the blood stream. Accordingly, the active substance may remain effective over a long period of time and out of the polysaccharide coating is allowed to gradually enter the tissue of the vessel. It has been demonstrated that significant concentrations of the active substance could still be detected after some weeks.

Polysaccharides constitute a hydrophilic coating that undergoes a certain swelling or softening process when existing in an aqueous environment such as blood. During balloon dilatation this results in the active substance to be properly transferred onto the inner wall of the vessel. The inventive method lends itself particularly well to the application of lipophilic coatings to the balloon. In fact, it has been found that hydrophilic polysaccharides in particular are well suited to cause lipophilic active substances to be effectively transferred during balloon dilatation to the inner walls of the vessels to be treated where they will bring about long-lasting active agent concentrations. It is assumed within the context of the inventive method that the water and/or at least one alcohol containing liquid will at first cause embrittlement of the active agent coating with the subsequently applied polysaccharide molecules settling between the active agent molecules and in this manner causing the active substances to be homogenously distributed within the polysaccharide matrix. In the balloons produced by the method proposed according to the invention the active substances are advantageously covered by the finally applied polysaccharide.

The term balloon as it is used within the scope of the present invention shall be understood to define the element of a balloon catheter that can be expanded by feeding in a fluid, irrespective of the form or material of said expandable element. Basically, balloon catheters are sufficiently known from prior art and comprise an elongated catheter probe extending from proximal to distal as well as a balloon which is arranged in the distal area. With respect to its dimensions such a catheter is suitably designed for the insertion into a body lumen, especially into a (blood) vessel system. The relevant dimensions of such catheters may vary depending on whether the blood vessel is, for example, a coronary artery, an intracranial blood vessel or an artery in the lower leg. Moreover, the balloon catheter is provided with means for supplying a fluid to the balloon. This may be a supply lumen extending over the length of the balloon catheter.

In addition, the inventive balloon catheter may not only be used for the local administration of active substances but also for the placement of a stent (endoprosthesis) in a body lumen. Stents are tube-like supporting structures implanted into a body lumen, for example a blood vessel, with a view to keeping it permanently open. Stents of this nature may be of self-expanding design or expanded with the help of a balloon. For this purpose, the stent is crimped onto the balloon and introduced into the body lumen with the aid of a balloon catheter. At the desired placement site the balloon is inflated by feeding in a fluid, which also causes the stent to expand and thus be anchored in the body lumen. Using the inventive balloon enables the relevant active substance to be applied at the same time to the wall of the body lumen. Finally, the balloon is deflated and removed from the body lumen whereas the stent remains in the body lumen.

The water and/or at least one alcohol containing liquid is, in particular, an aqueous solution containing an alcohol and/or ketone. The concentration of the alcohol and/or ketone in the aqueous solution typically ranges between 10 and 70% (v/v), preferably between 30 and 65% (v/v), further preferred between 50 and 60% (v/v), and especially preferred is approx. 55% (v/v). Basically suitable are alcohols and ketones that can be mixed with water, wherein a blend consisting of several alcohols and/or ketones may also be employed, in which case the above named preferred concentration details shall apply as a whole. Preferred is the use of ethanol, methanol, acetone and/or isopropanol, with ethanol being mostly preferred. Moreover, the aqueous solution may comprise an azeotropic solvent blend, in particular an alcohol/water mixture, with an ethanol/water mixture being preferred. Also conceivable is to provide the water and/or at least one alcohol containing liquid with an additional amount of active agent to increase the amount of active substances present on the balloon.

In the method provided by the invention the surface of the balloon is at least partially wetted with a first solution of an active agent. Subsequently, the part of the balloon surface wetted with said first solution of an active agent is wetted with a water containing and/or at least one alcohol containing liquid.

By wetting the surface of the balloon with said first solution of an active agent, a lacquer-like transparent coat of the active substance is formed on the surface, said coat or layer forming the basis for a homogenous and reproducible active agent loading. While the wetting process takes place the balloon material, in particular when methylene chloride is used, is capable of absorbing a solvent which under normal conditions is then released in a few hours.

The coating produced by treating the balloon with the first solution will be attacked by the water and/or at least one alcohol containing liquid making the surface partially more porous or causing it to become brittle. The entire coating becomes more brittle and less transparent visually, that is it looks milkier. The surface so produced has a chalk-like possibly even a non-crystalline consistency allowing a higher degree of active substances release or removal under friction than can be achieved with a coating produced by wetting the surface of the balloon only with the first solution of the active agent.

The polysaccharide in the further solution shall preferably exist in an alcohol containing solution as well. Aside from one or several alcohols this solution may in particular also contain water. An aqueous-alcoholic solution offers advantages in that it allows the polysaccharide to be well dissolved but does not affect or remove the already applied active agent coat. Moreover, the content of organics in the solution enables a rapid drying process to take place after wetting. The concentration of the alcohol or alcohols in the further solution typically ranges between 10 and 70% (v/v), preferably between 30 and 65% (v/v), further preferred between 50 and 60% (v/v), and especially preferred is approx. 55% (v/v). Suitable alcohols are those that are capable of dissolving polysaccharide. As a rule, such alcohols can also be mixed with water. Preferred are ethanol, methanol, and isopropanol, with ethanol being especially preferred.

Expediently, the mean molar mass of the polysaccharide ranges between 10,000 and 100,000,000 Da. A mean molar mass of between 20,000 and 80,000 Da has proved to be especially suitable for the purpose. Branched polysaccharides are preferred. The content of polysaccharides of the further solution preferably amounts to between 1 and 15% (w/w), further preferred between 2 and 10% (w/w), and especially preferred between 3 and 8% (w/w).

Preferably, the polysaccharide is a branched polysaccharide. Also suitable are mixtures composed of several polysaccharides and modified polysaccharides. Preferred are dextrans, in particular natural dextrans. Dextrans are high-molecular, branched polymers composed of glucose units. They are produced, inter alia, by bacteria of genus *Leuconostoc* and used as blood plasma substitutes or as carriers in the field of chromatography.

The dextran used may in particular be a natural dextran, and especially preferred is dextran 40 having a mean molar mass of approx. 40,000 Da.

However, aside from dextrans other polysaccharides may basically be employed as well. An example of a modified polysaccharide that can be used is hydroxyethyl starch (HES).

In principle, either the entire balloon surface or only part of said balloon surface, for example only that area of the surface that will have contact with the tissue when the balloon has been inflated, can be coated by the inventive method. The balloon may, in particular, have a cylinder-shaped area and at least one tapering/conical area. In this case, for example, only the cylinder-shaped portion of the balloon may be coated with an active substance in accordance with the invention or the cylinder-shaped portion and a conical area.

With regard to the active agent the first solution may be saturated. Solvents that can be employed are, for example, methylene chloride, chloroform, alcohol, in particular ethanol, methanol or isopropanol, acetone, diethyl ether, liquid hydrocarbons, such as, for example, pentane, hexane, heptane, cyclohexane or octane, toluol, tetrahydrofuran (THF) or ethyl acetate. Furthermore, solvent mixtures or blends may also be employed. This preferably concerns a solution of the active agent in methylene chloride.

Wetting the surface of the balloon with a liquid (first solution, water and/or at least one alcohol containing liquid or a further solution containing a polysaccharide) may in any case be brought about by immersing the balloon into the liquid. As a rule, the balloon is immersed for a maximum period of 1 min., typically for 10 to 30 s, with the balloon being in at least partially expanded state during immersion. The immersed balloon should then be drawn out of the first solution at a speed of up to 10 mm/s. Even more favorable would be to withdraw the balloon at a speed of less than 5 mm/s, preferably at a speed ranging between 0.5 mm/s and 2 mm/s. Withdrawing the balloon slowly enables the surface to dry gradually and slowly.

As an alternative to wetting the balloon by immersion other methods may also be adopted, for example spraying.

Moreover, before being wetted with the first solution of an active agent the surface of the balloon may be cleaned and/or provided with structuring or given a profiled contour. The balloon surface may, for example, be structured or profiled mechanically, thermally or chemically. Such structuring or profiled contour may be brought about in particular by roughening the surface. Advantageously, cavities having a depth of between 5 and 50 µm and a diameter ranging between 5 and 50 µm are thus created on the surface by such an enlargement of the balloon surface. The profiled contour ensures that the active agent as well as the polysaccharide are absorbed better.

Moreover, having been wetted with the first solution of the active agent and before being wetted with the water and/or at least one alcohol containing liquid the surface of the balloon may also be wetted with an additional solution containing the same active agent. In this manner, the active agent load will be increased. Wetting the surface with said additional solution may also bring about an at least partial embrittlement of the entire coating. The entire coating may as well become less transparent visually and thus look milkier. On the whole it can be said, wetting the surface with said additional solution of the active agent enables a higher active agent release under friction in comparison to the lacquer-like surface created by wetting with the first solution.

Basically, the balloon may be wetted with as many additional solutions as desired of which not all need contain the active agent. If thought expedient, an additional solution may also contain another type of active agent.

For example, said additional solution may contain the active agent dissolved in methylene chloride. Preferably, the concentration of the solution should be lower than that of the first solution, for example 100 mg/ml. Other solvents such as for example chloroform or ethanol or solvent mixtures may be employed as well. The surface of the balloon can be wetted by immersing the balloon into the additional solution while other techniques, for example spraying, may also be applied, however.

The surface of the balloon may, furthermore, be dried after wetting it with the first solution, wetting with the additional solution, wetting with the water and/or at least one alcohol containing liquid, and/or wetting with the further solution containing a polysaccharide. For example, the balloon may have a longitudinal axis and be rotated around its longitudinal axis during the drying process. To achieve a drying effect as uniform as possible, the longitudinal axis of the balloon can be positioned horizontally immediately after wetting has been completed. The balloon can then be rotated in a stream of air around its longitudinal axis.

The active agent used is, in particular, a drug or medical substance that has a proliferation-inhibiting effect preventing a vasoconstrictive overgrowing of the vessel location previously expanded by the balloon. The active agent may in particular be selected from the following: Tretinoin, orphan receptor agonists, elafin derivatives, corticosteroids, steroid hormones, paclitaxel, rapamycin, tacrolimus, hydrophobic proteins as well as substances modifying cell proliferation. Mixtures of these active substances may also be used. Moreover, derivatives of the above cited active agents may also be of use, wherein said derivatives may in particular be salts, esters, and amides. As steroid hormones methylprednisolone, dexamethasone or estradiol may be employed, for example. Especially preferred is the use of paclitaxel or paclitaxel derivatives.

Coating the balloon with the active agent preferably takes place without solutizers being used. Solutizers for example are: Phosphatidylcholine, polyethoxylated castor oil, cardiolipin, cholesterol as well as mixtures thereof.

The inventive balloon of a balloon catheter comprises a surface that at least in part is provided with a coating containing the active agent. In the entirety of the coated area said coating is of homogenous and brittle characteristic, wherein on the outside of the coating an overlay comprising the applied polysaccharide is arranged. The polysaccharide thus covers both the active agent and the balloon. The surface may in particular have a chalk-like and, as the case may be, also a non-crystalline structure. Furthermore, the surface of the balloon may be coated either completely or only in part. In particular, the balloon may have a cylinder-shaped area and at least one tapering/conical area. In this case, for example, only the cylinder-shaped part of the balloon or the cylinder-shaped portion and a conical area may be coated with an active substance in accordance with the invention. The inventive balloon can be manufactured by means of the inventive method. It warrants a homogenous and high drug release to the surrounding tissue in the body, which is kept effective over a long period due to the polysaccharide comprising coat arranged on the outside.

The balloon catheter according to the invention comprises the inventive balloon and offers the same advantages as the inventive balloon.

PREFERRED EMBODIMENTS

Example

A customary balloon of a balloon catheter is pre-cleaned initially. The expanded balloon is immersed into a solution of paclitaxel in methylene chloride. The concentration of paclitaxel amounts to 200 mg/ml while the immersion time is 10 s. Subsequently, the slowly withdrawn balloon is allowed to dry for a period of 30 s.

In a second step, the balloon is immersed in expanded state into an aqueous ethanol solution (55% (v/v)) for a period of 30 s. Following this, a drying time of 120 s is to be allowed.

In a third step, the balloon is immersed in expanded state into a dextran solution for a period of 10 s, with the dextran being dissolved in aqueous ethanol (55% (v/v)).

All steps are carried out at room temperature.

The results can be seen in the attached figures.

Figure 1:
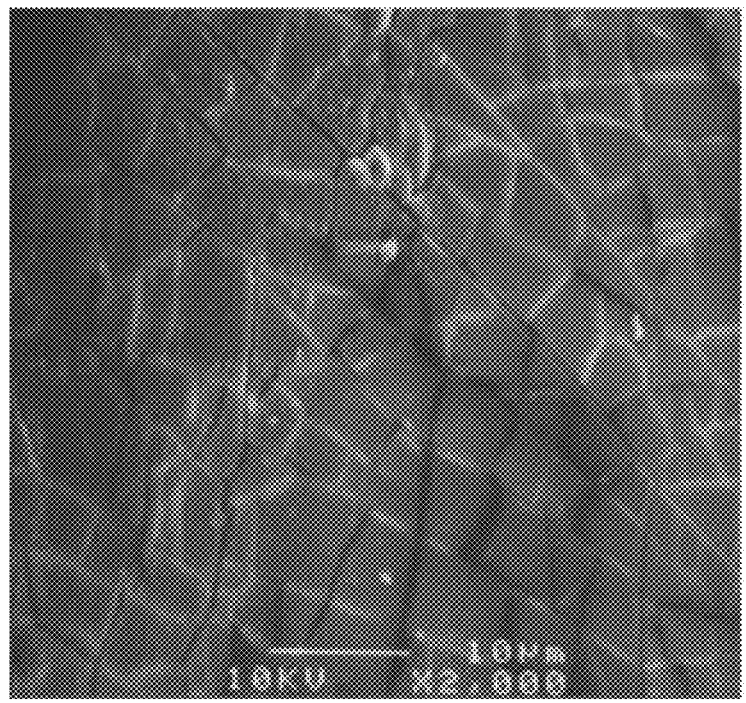
FIG. 1 shows an electron microscope image of a coating produced from the first solution.
Figure 2:
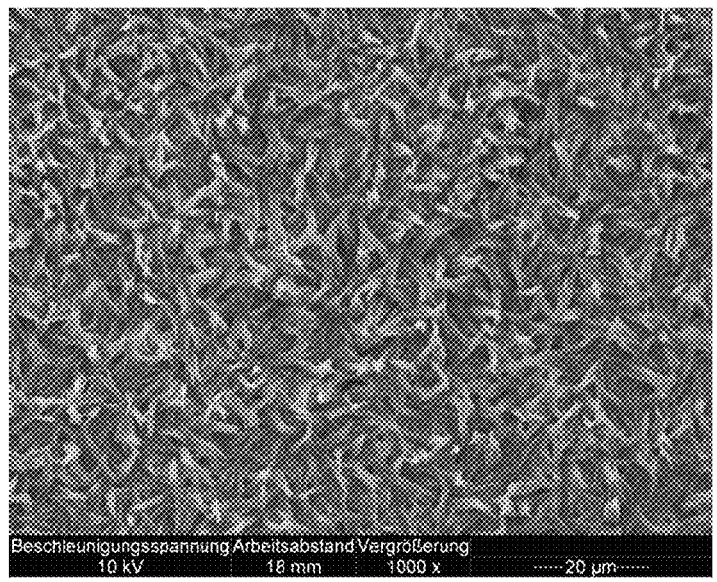
FIG. 2 shows an electron microscope image of the coating after immersion in the second solution.

It is shown in:

FIG. 1: an electron-microscope produced image of the coating after immersion into a first solution and FIG. 2: an electron-microscope produced image of the coating after immersion into the water and/or at least one alcohol containing liquid.

FIG. 1 shows the surface of a balloon catheter after immersion into the first solution that contains the active agent. It is an image produced by means of an electron microscope from which a lacquer-like surface can be seen.

FIG. 2 shows the same surface after immersion into an aqueous ethanol solution (55% (v/v)). It can be seen that the surface is more brittle which results in an improved active agent release to the vessel wall.

What is claimed is:

1. A method for coating a balloon of a balloon catheter, the method comprising:
    applying an active agent coating to at least a part of a surface of the balloon by wetting with a first solution of an active agent;
    wetting the active agent coating on the part of the surface of the balloon, wetted with the first solution, with a second solution that is a liquid containing water and/or at least one alcohol and/or at least one ketone;
    subsequently applying a dextran coating as a cover coating onto the wetted active agent coating by wetting with a third solution, containing dextran and being free of the active agent, and preparing the third solution to contain one or more alcohols.

2. The method according to claim 1, further comprising selecting a concentration of the at least one alcohol and/or the at least one ketone in the liquid to be in a range from 10% (v/v) to 70% (v/v).

3. The method according to claim 2, wherein the concentration of the at least one alcohol and/or the at least one ketone in the liquid is selected to be in a range from 30% (v/v) to 65% (v/v).

4. The method according to claim 3, wherein the concentration of the at least one alcohol and/or the at least one ketone in the liquid is selected to be in a range from 50% (v/v) to 60% (v/v).

5. The method according to claim 1, further comprising preparing the liquid to contain at least one compound of the group consisting of ethanol, methanol, acetone, and isopropanol.

6. The method according to claim 1, further comprising selecting a concentration of the one or more alcohols in water in the third solution to be in a range from 10% (v/v) to 70% (v/v).

7. The method according to claim 6, wherein the concentration of the one or more alcohols in water in the third solution is selected to be in a range from 30% (v/v) to 65% (v/v).

8. The method according to claim 7, wherein the concentration of the one or more alcohols in water in the third solution is selected to be in a range from 50% (v/v) to 60% (v/v).

9. The method according to claim 1, further comprising preparing the third solution to contain at least one compound of the group consisting of ethanol, methanol, and isopropanol.

10. The method according to claim 1, further comprising selecting a mean molar mass of the dextran to be approximately 40,000 Da.

11. The method according to claim 1, further comprising selecting the active agent of the first solution from the group consisting of tretinoin, orphan receptor agonists, elafin derivatives, corticosteroids, steroid hormones, paclitaxel, rapamycin, tacrolimus, hydrophobic proteins, and substances modifying cell proliferation.

12. The method according to claim 1, wherein the step of applying an active agent coating includes wetting the part of the surface of the balloon, after wetting with the first solution and before wetting with the second solution, with a fourth solution containing an active agent, wherein the active agent is the same as the active agent of the first solution or is different from the active agent of the first solution.

13. A balloon of a balloon catheter comprising a surface coated by the method of claim 1.

14. A balloon catheter comprising a balloon comprising a surface coated by the method of claim 1.

* * * * *